(12) United States Patent
Forssmann

(10) Patent No.: US 8,293,711 B2
(45) Date of Patent: Oct. 23, 2012

(54) USE OF NATRIURETIC PEPTIDES FOR TREATING ANGIOEDEMA SYNDROMES

(75) Inventor: Wolf-Georg Forssmann, Wies-Wambach (DE)

(73) Assignee: Pharis Biotech GmbH, Hannover (DE)

( * ) Notice: Subject to any disclaimer, the term of this patent is extended or adjusted under 35 U.S.C. 154(b) by 75 days.

(21) Appl. No.: 12/733,609

(22) PCT Filed: Sep. 11, 2008

(86) PCT No.: PCT/EP2008/062067
§ 371 (c)(1),
(2), (4) Date: Mar. 11, 2010

(87) PCT Pub. No.: WO2009/034134
PCT Pub. Date: Mar. 19, 2009

(65) Prior Publication Data
US 2010/0204446 A1 Aug. 12, 2010

(30) Foreign Application Priority Data

Sep. 11, 2007 (EP) .................................. 07116164
Jan. 8, 2008 (EP) .................................. 08100213

(51) Int. Cl.
*A61K 38/16* (2006.01)
*A61K 38/17* (2006.01)
(52) U.S. Cl. .................................................... 514/12.4
(58) Field of Classification Search .................. None
See application file for complete search history.

(56) References Cited

U.S. PATENT DOCUMENTS 5,571,789 A 11/1996 Fluge et al.
6,831,064 B1 12/2004 Forssmann et al.

FOREIGN PATENT DOCUMENTS

| EP | 0 369 474 | 5/1990 |
| WO | WO 88/06596 | 9/1988 |
| WO | WO 2004/022579 | 3/2004 |
| WO | WO 2006/110743 | 10/2006 |

OTHER PUBLICATIONS

Brunner-La Rocca et al. Cardiovascular Research 51: 510-520, 2001.*
Mitrovic et al. American Heart Journal 150: 1239.e1-1239.e8, 2005.*
Dobrivojevic et al. BMC Pharmacology 11(Suppl 1): P21, 2011.*
Elsner et al. "Efficacy of prolonged infusion of urodilatin [ANP-(95-126)] in patients with congestive heart failure." American Heart Journal, vol. 129, No. 4, Apr. 1995, pp. 766-773.
Dorner et al. "Hemodynamic effects of continuous urodilatin infusion: A dose-finding study." Clinical Pharmacology and Therapeutics, vol. 64, No. 3, 1998, pp. 322-300.
Kentsch et al. "Haemodynamic and renal effects of urodilatin bolus injections in patients with congestive heart failure." European Journal of Clinical Investigation, vol. 22, No. 10, 1992, pp. 662-669.
Kentsch et al. "Severe hyptension and bradycardia after continuous intravenous infusion of urodilatin (ANP 95-126) in a patient with congestive heart failure." European Journal of Clinical Investigation, vol. 25, 1995, pp. 281-283.
Flattery et al. "Angiotensin-Converting enzyme inhibitor-related angioedema: recognition and treatment." Progress in Cardiovascular Nursing, vol. 22, No. 1, 2007, pp. 47-51.
SICA "Angiotensin-Converting Enzyme Inhibitors Side Effects—Physiologic and Non-Physiologic Considerations." The Journal of Clinical Hypertension, vol. 6, No. 7, Jul. 2004, pp. 410-416.
Campbell "Hypertension." American Heart Association, vol. 41, 2003, pp. 383-389.
Hedner et al. "Angio-oedema in relation to treatment with angiotensin converting enzyme inhibitors." Br. Medical Journal, vol. 304, 1992, pp. 941-946.
Cupido et al. "Life-threatening angio-oedema and death associated with the ACE inhibitor enalapril." S. African Medical Journal, vol. 97, No. 4, 2007 pp. 244-245.
Schuster et al. "Angioodem unter ACE-Hemmern und Angiotensin-II-Rezeptor-Antagonisten: Analyse von 98 Fallen." Schweiz Med Wochenschr, vol. 129, No. 9, (1999), pp. 362-369.
ASERO "Use of ketoprofen oral challenges to detect cross-reactors among patients with a history of aspirin-induced urticaria." Ann. Allergy Asthma Immunol., vo. 97, No. 2, 2006, pp. 187-189.
Frith et al. "Life threatening asthma, urticaria, and angioedema after ketoprofen." vol. 14, No. 2, 1978, pp. 847-888.
Davis. "Mechanism of angioedema in first complement component inhibitor deficiency." Immunology and Allegery Clinics of North America, vol. 26, No. 4, 2006, pp. 633-651.
Agostoni et al. "Hereditary and Acquired C1-Inhibitor Deficiency: Biological and Clinical Characteristics in 235 patients." Medicine, vol. 71, No. 4, 1992, pp. 206-215.
Longhurst et al. "C1-inhibitor concentrate home therapy for hereditary angioedema: a viable, effective treatment option." Clinical and Experimental Immunology, vol. 147, 2006, pp. 11-17.
Sano et al "Arteriosclerosis, Thrombosis, and Vascular Biology." American Heart Association, vol. 26, 2006, pp. 2673-2680.
Kim et al. "Genetic mechanism of aspiring-induced urticari/angioedema." Current Opinion in Allergy and Clinical Immunology, vol. 6, No. 4, 2006, pp. 266-270.
Marshall et al. "Angioedema associated with aspirin and rofecoxib." The Annal of Pharmacotherapy, vol. 39, No. 5, 2005, pp. 944-948.
Grzelweska-Rzymowska et al "Aspirin <<description>> in patients with aspiring-induced urticaria and angioedema." Allergol et Immunopathol, vol. 15, No. 5, 1988, pp. 305-308.
Higashi et al. "Aspirin-induced urticaria and angioedema, but not bronchoconstriction, associated with cysteinyl leukotriene overproduction in 2 patients with asthma." Allergy Clinical Immunology, vol. 110, No. 4, 2002, pp. 666-667.

* cited by examiner

*Primary Examiner* — Christine J Saoud
(74) *Attorney, Agent, or Firm* — Jacobson Holman, PLLC

(57) ABSTRACT

The present invention relates to the use of a natriuretic peptide, urodilatin, for treating patients suffering from acute drug induced angioedema, such as ACE inhibitor related adverse events. Preferably, a composition comprising an effective amount of urodilatin is intravenously administered to the patient continuously for 18 hours to 72 hours.

11 Claims, 5 Drawing Sheets

USE OF NATRIURETIC PEPTIDES FOR TREATING ANGIOEDEMA SYNDROMES

This is a national stage of PCT/EP08/062067 filed Sep. 11, 2008 and published in English, which has a priority of European no. 07116164.0 filed Sep. 11, 2007 and priority of European no. 08100213.1 filed Jan. 8, 2008, hereby incorporated by reference.

The present invention relates to the use of a natriuretic peptide for the manufacture of a medicament for the treatment of angioedema.

Natriuretic peptides are a family of related peptides that regulate salt and water balance in the body. These peptides are originated in different tissues, have slight variations in their amino acid sequence and in their capability to induce natriuresis and diuresis in the kidney. 4 members are known in the human body: atrial natriuretic peptide (ANP), brain natriuretic peptide (BNP), C-type natriuretic peptide (CNP), and urodilatin (URO, or ularitide). While ANP and BNP are distributed in the heart and brain, CNP is released from the brain and endothelial cells and urodilatin from the kidney. These peptides are part of a hormonal system that keeps a fine balance of water and blood volume and pressure in the body. Urodilatin, secreted directly by kidney cells, is one of the hormones responsible for the inhibition of water and $Na^{3O}$- reabsorption in the kidney's collecting duct. Urodilatin is also known for its heart protective abilities and has been studied for the use in treatment of renal failure and congestive heart failure (U.S. Pat. No. 5,571,789; U.S. Pat. No. 6,831,064; Elsner et al., *Am. Heart J.* 1995, 129(4):766-773; Forssmann et al., *Clinical Pharmacology and Therapeutics* 1998, 64(3): 322-330); Kentsch et al., *Eur. J. Clin. Invest.* 1992, 22(10): 662-669; Kentsch et al., *Eur. J. Clin. Invest.* 1995, 25(4):281-283).

Besides natriuretic peptides ACE inhibitors and angiotensin II-receptor blockers are used as therapeutic drugs in patients with hypertension and congestive heart failure. But an often under-recognized side effect of ACE inhibitors as well as angiotensin II receptor antagonists is the development of angioedema. This is a particularly important side effect to realize since it can be life threatening if not treated properly. The term angioedema is used to describe an abrupt and short lived swelling of the skin, mucuos membranes including upper respiratory and oropharyngeal areas. Although it can occur in any part of the body, it most frequently involves the head, neck, lips, mouth, tongue, larynx, pharynx, and subglottal areas and rarely accompanied with urticaria. It has been demonstrated that bradykinin levels were 12-fold increased during acute angioedema attacks (heredetary or acquired). ACE-Inhibitors extend the vasodilating effect of bradykinin due to the inhibition of its breakdown (Flattery and Sica, *Prog. Cardiovasc. Nurs.* 2007, 22(1):47-51; Sica, *J. Clin. Hypertens.* 2004, 6(7):410-416; Campbell, *Hypertension*, 2003, 41:383-389; Hedner et al., *Br. Med. J.,* 1992, 304:941-946; Cupido and Rayner, *S. Afr. Med. J,* 2007, 97(4): 244-245).

The Swiss Drug Monitoring Center (SANZ) reported on 98 cases of drug-induced angioedema, 94 cases of ACE inhibitor-induced and 4 cases of angiotension II-receptor antagonist-induced angioedema. 28 of these cases were classified severe and in three patients even intubation was required. The occurrence of angioedema varied from a few days to several months. In one case a latency of 8 years was recorded, demonstrating that this kind of adverse drug reaction is actually hard to be detected. During the administration of ACE-inhibitors edema could recur for up to 20 times. Angiotensin II receptor antagonists (ARB) are also capable of introducing angioedema, but the course is usually milder (Schuster et al., Schweiz. *Med. Wochenschr.,* 1999, 129(9):362-369). This might be due to the fact that ARB inhibits the VEGF-induced vascular hyperpermeability (Sano et al., *Arterioscl. Thromb. Vasc. Biol.,* 2006, 26:2673-2680) but increase the bradykinin-induced angioedema.

Besides ACE inhibitors and angiotensin II-receptor antagonists there are also reports on other mechanisms for drug-induced angioedema. Among those are cyclooxygenase inhibitors, such as Aspirin (COX-1 inhibitor) and rofecoxib (COX-2), which are known to induce asthma, urticaria and angioedema. The aspirin-induced angioedema is an aspirin-related hypersensitivity that is often associated with aspirin-intolerant asthma, which causes chronic overproduction of cysteinyl leukotrienes. Ketoprofen, another non-opiod analgetic, inhibits prostaglandins and thus, the production of cyclooxygenase, is also known for inducing life-threatening asthma, urticaria and angioedema (Kim et al., *Curr. Opin. Allergy Clin. Immunol.,* 2006, 6(4):266-270; Marshall, *Ann. Pharmacother.,* 2005, 39(5):944-908; Grzelewska-Rzymowska et al., *Allergol. Immunopathol.* (Madrid), 1988, 16(5):305-308; Higashi et al., *Allergy Clin. Immunol.,* 2002, 110(4):666-667; Asero, *Ann. Allergy Asthma Immunol.,* 2006, 97(2):187-189; Frith et al., Lancet, 1978, 14(2):847-888).

Hereditary and acquired angioedemas can also result from a deficiency of the first complement component (C1)- or plasma protease inhibitor. The most obvious role of the C1-Inhibitor is the prevention of excessive vascular permeability where bradykinin is a key player. The lack of this enzyme leads to recurrent subcutaneous and submucosal angioedema. Acquired C1-esterase inhibitor deficiency has been observed in association with lymphoproliferative disorders, malignancy, autoimmune diseases and infections (Davis, *Immunol. Allergy Clin. North Am.,* 2006, 26(4):633-651; Agostoni and Cicardi, *Medicine* (Baltimore), 1992, 71(4):206-215; Longhurst et al., *Clin. Exp. Immunol.,* 2006, 147:11-17).

Angioedema is an underestimated clinical problem, since many cases are nonallergic reactions such as bradykinin-induced angioedema caused either by genetic defects or by ACE-inhibitors. Some angioedema which manifest in the larynx are life threatening. The vast majority of angioedema are caused by ACE-inhibitors blocking the renin-angiotensin-aldosterone system (RAAS). So far ACE inhibitors and angiotensin II antagonists are the drugs of choice for patients associated with cardiovascular diseases, which constitute the leading cause of death in the United States regardless of gender or ethnicity. Among these diseases, congestive heart failure (CHF) is of particularly high prevalence. This life-threatening condition is accompanied by great financial impact. So far, ACE inhibitors and angiotensin II-antagonists have been used to counteract this threat more or less successfully. Both groups of inhibitors are known to induce yet another threat, angioedema, ACE inhibitors more than AII-antagonists. Angioedema can lead to rapid swelling of the skin, mucosa and submucosal tissue and becomes life-threatening whenever airway obstruction and suffocation occurs.

Thus, there is a new strong need for providing new and more effective methods for treating heart failure without the negative side effects of angioedema.

This problem is solved by the natriuretic peptides of this invention.

Therefore, it is one object of this invention to provide a natriuretic peptide, in particular Urodilatin, for the manufacture of a medicament for the treatment of angioedema. The present invention represents a novel inventive procedure for treating angioedema in patients suffering from this syndrome of different etiologies. This method is substantiated by intravenously applying an adequately effective concentration of urodilatin (ularitide) to acutely appearing oedema. The infusion may be continuous for at least 24 hours. The treatment method also implies that an initial bolus infusion of a natriuretic peptide, in particular urodilatin, may be used in special cases, when the risk of potential impairment of kidney function is relatively low compared to the expected benefit.

Figure 1:
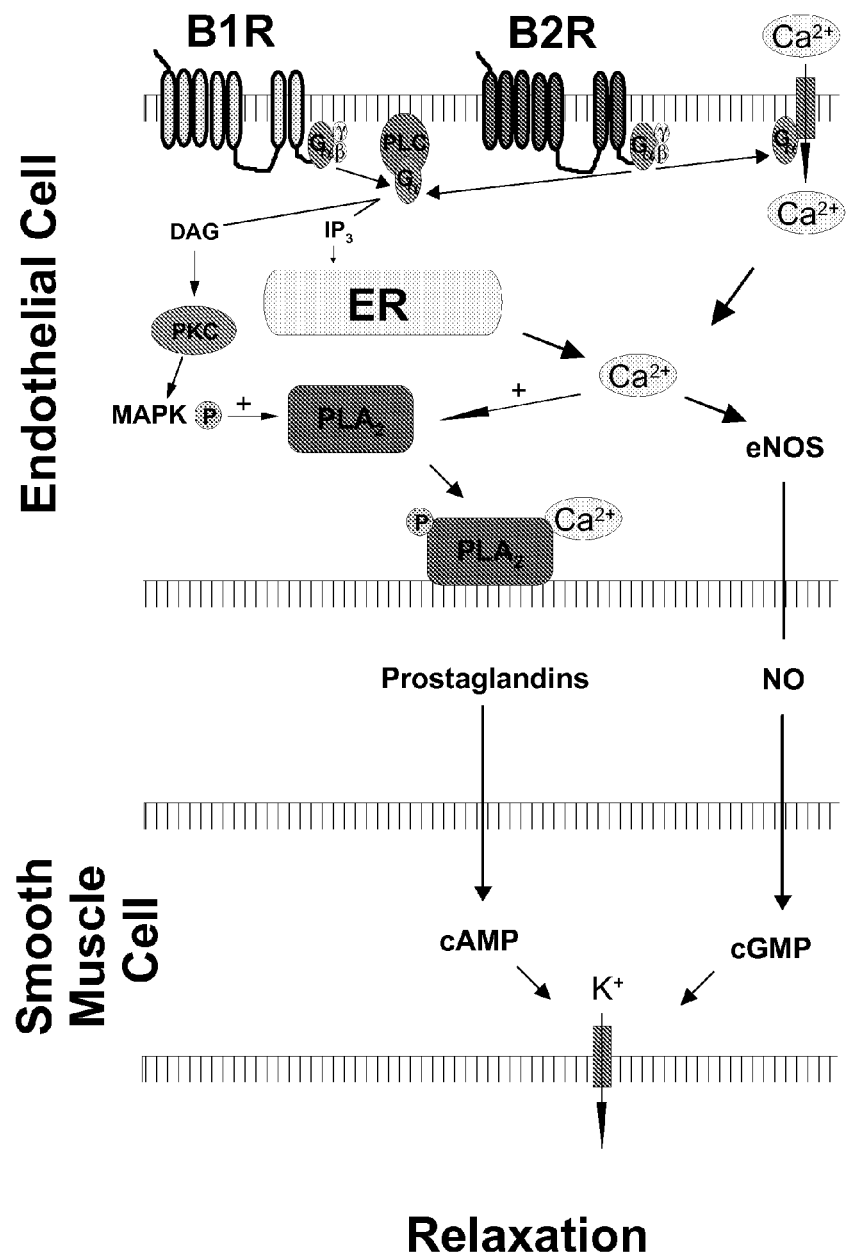
FIG. 1 is a schematic representation of the signaling pathways of bradykinin through receptor types B1R and B2R.

Thus Urodilatin may exceptionally been given to angioedema patients by a high dose intravenous bolus application or a short-lasting high dose infusion for one hour then followed by an intravenous dose infusion of moderate concentration only in deleterious cases of syndrome. Urodilatin application induces strong diuretic and natriuretic effects in acute renal failure models and displays beneficial hemodynamic effects resulting in a volume redistribution favorable in angioedema whereby a withdrawal of fluid from interstitial tissues is observed. As a vasodilator that relaxes both arterial and venous blood vessels it reduces the pre- and after load of the heart. Together with its diuretic capability it counteracts existing edema as well as the regeneration of edema. Furthermore, as a bronchodilator it also improves bronchial asthma and other obstructive pulmonary diseases often accompanied with angioedema. Responsible for the drug-induced angioedema are the up regulation of B1- and B2-receptors and thus, the prolonged bradykinin response. The bradykinin effect responsible for the generation of edema is tyrosine kinase mediated. Urodilatin shows counter-regulatory effects towards bradykinin in bronchi and inhibits the tyrosine kinase activated pathway by bradykinin explaining its positive effect on ACE-induced angioedema.

Natriuretic peptides, such as Urodilatin, are further effective in treating heart failure patients. A new method for administering urodilatin that is surprisingly effective for the purpose of treating angioedema is one further embodiment of the present invention.

As used herein, the term "angioedema" encompasses all types of cardiovascular conditions that, regardless of their cause, are generally recognized by a physician as angioedema, which includes but are not limited to hereditary angioedema, acquired angioedema, and particularly drug-induced angioedema. These conditions typically involve weakened heart function combined with a build-up of body fluid resulting in abrupt and short lived swelling of the skin, mucuos membranes including upper respiratory and oropharyngeal areas. Although it can occur in any part of the body, it most frequently involves the head, neck, lips, mouth, tongue, larynx, pharynx, and subglottal areas and rarely accompanied with urticaria.

In one embodiment of the invention, the natriuretic peptide is urodilatin. Further, the natriuretic peptide can be selected from the group consisting of ANP, BNP and CNP.

In one particular embodiment the natriuretic peptide of the invention is further used for the manufacture of a medicament for the treatment of heart failure.

In one additional aspect, said medicament is administered intravenously at the rate of at least 7.5 ng/kg/min and up to a maximal rate of 60 ng/kg/min.

In another aspect of the invention, said medicament further comprises mannitol, in particular 3 to 10% or 4 to 8% of mannitol respective to the final infusion solution.

In one embodiment of the invention said medicament further comprises NaCl, in particular 0.9% of NaCl respective to the final infusion solution. Further, the final infusion solution can be reconstituted with other aqueous inactive ingredients used in standard medical praxis.

In another embodiment, the medicament is administered for a time period of at least 24 hours, or of 18 to 24 hours, or 24 to 72 hours, or for more than 72 hours.

In a particular aspect, the natriuretic peptide is further used for the manufacture of a medicament for the treatment of drug-induced angioedema provoked by inhibitors of angiotensin converting enzyme. Toxic substances ingested in nutrition and others can also induce the drug-induced angioedema.

In order to understand the possible mechanism by which urodilatin prevents and reduces angioedema, one has to understand the various signal pathways of bradykinin, which is the main responsible factor for hereditary and acquired angioedema. Bradykinin acts through two different forms of receptors, B1R and B2R, which both couple to similar signal transduction pathways but differ in terms of variation of $Ca^{2+}$ concentration. B1R is mainly associated with PLC activation and the phosphoinositol pathway but can also act through PLA2 and MAP kinase pathways. The activated $Ca^{230}$ pathways in endothelial cells lead to activation of prostaglandins and to a rise in cAMP levels in smooth muscle cells. Furthermore, eNOS is activated and releases NO which increases cGMP levels in smooth muscle cells. Both processes are responsible for the relaxation of smooth muscle cells (see FIG. 1). While B2R can be desensitized by phosphorylation of specific serine and tyrosine residues in the C-terminal domain, B1R lacks any of these residues and cannot be down regulated except for endocytosis processes. In the hereditary angioedema (HAE) the C1-Inhibitor is either not functional or not present at all leading to a continuous release of bradykinin and an increased vascular permeability. Inhibition of B2R by specific antagonists such as HOE-140, reveres the increased permeability. In the acquired form of angioedema the natural breakdown of bradykinin is prevented, e.g. by ACE-inhibitors since the angiotensin 1 converting enzyme among other things inactivates bradykinin. While a B2R antagonist is effective in the HAE, it is less effective in the acquired form of angioedema and other bradykinin-related forms of edema. In vivo studies demonstrated that the up regulation of B1R led to the release of cytokines, activation of PKC and tyrosine kinase pathways including MAP kinase and NFκB, and subsequently to the formation of edema. Quite recently it could be shown that bradykinin and substance P-induced edema in the hamster cheek pouch is tyrosine kinase dependent and the bradykinin-mediated effect could be attenuated using the unspecific tyrosine kinase inhibitors genistein and tyrphostin 25.

CNP, a member of the natriuretic peptide family, does not only use the familiar cGMP signaling pathway but can also bind to a receptor that lacks guanylate cyclase activity but acts as a tyrosine kinase, named NPR-Bi. The human embryonic kidney cell line HEK-293 displays many features of the late tubule of the kidney and have the ability of releasing urodilatin. In these cells it was shown that ANP/urodilatin is able to counteract tyrosine phosphorylation via activation of a cGMP-dependent pathway.

This leaves several possibilities how urodilatin can interact with the bradykinin signaling pathway in an inhibitory fashion: 1) Urodilatin could be a direct B1R receptor antagonist. 2) Urodilatin can desensitize B2R through phosphorylation by a cGMP-dependent protein kinase (PKG) at the specific serine residue or through tyrosine phosphorylation at the according tyrosine residue using an NPRi-like receptor pathway. 3) Urodilatin can interfere with the B1R pathway by activating MAP kinase-directed phosphatases and thus, inactivating specific MAP-kinases through phosphorylation processes by PKG. 4) Urodilatin can activate cAMP-specific phosphodiesterases through PKG activation and thus, limiting the bradykinin-activated $PLA_2$-response (see FIG. 2-5). 5) PKG phosphorylation can counter regulate the target ion channel in smooth muscle cells that is tyrosine phosphorylated.

While the B2R pathway is responsible for the antihypertensive, antihypertrophic and antiproliferative effects of ACE-inhibitors and the formation of hereditary angioedema, the B1R signaling pathway seems to be mainly responsible for inflammatory reactions, asthma and allergy, sepsis, brain edema and drug-induced angioedema.

FIG. 1: Schematic representation of the signaling pathways of bradykinin through the receptor types B1R and B2R. ER: endothelial reticulum; PLC: phospholipase C; DAG: diacylglycerol; $IP_3$: inositol 1,4,5-triphosphate; $PLA_2$: phospholipase $A_2$; NO: nitric oxide; eNOS: endothelial NO synthase.

Figure 2:
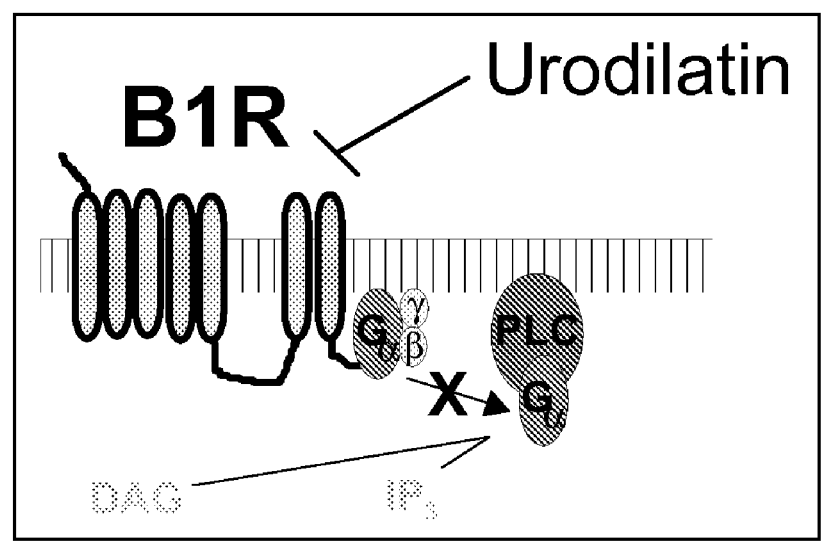
FIG. 2 is a schematic representation of how urodilatin acts as a receptor antagonist for B1R and blocks downstream signaling.

FIG. 2: Urodilatin acts as a receptor antagonist for B1R and blocks downstream signaling.

Figure 3:
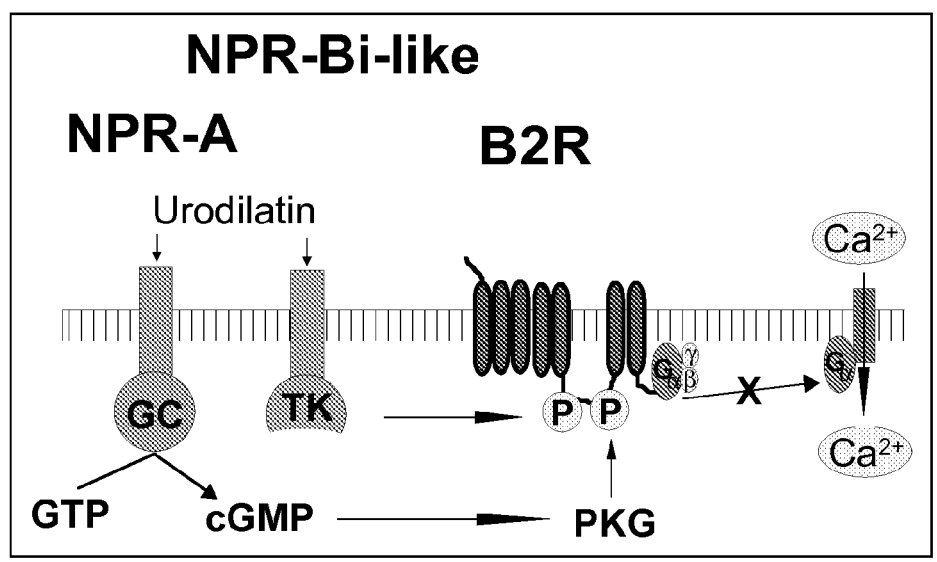
FIG. 3 is a schematic representation of how urodilatin desensitizes the B2R bradykinin receptor and blocks downstream signaling.

FIG. 3: Urodilatin desensitizes the B2R bradykinin receptor and blocks downstream signaling through a) the NPR-A receptor and activation of a cGMP-dependent protein kinase (PKG) and subsequent phosphorylation of a serine residue of the B2R; b) a NPR-Bi-like receptor which acts as a tyrosine kinase and phosphorylates a tyrosine residue on the B2R. In both cases the receptor is inactive for further bradykinin binding.

Figure 4:
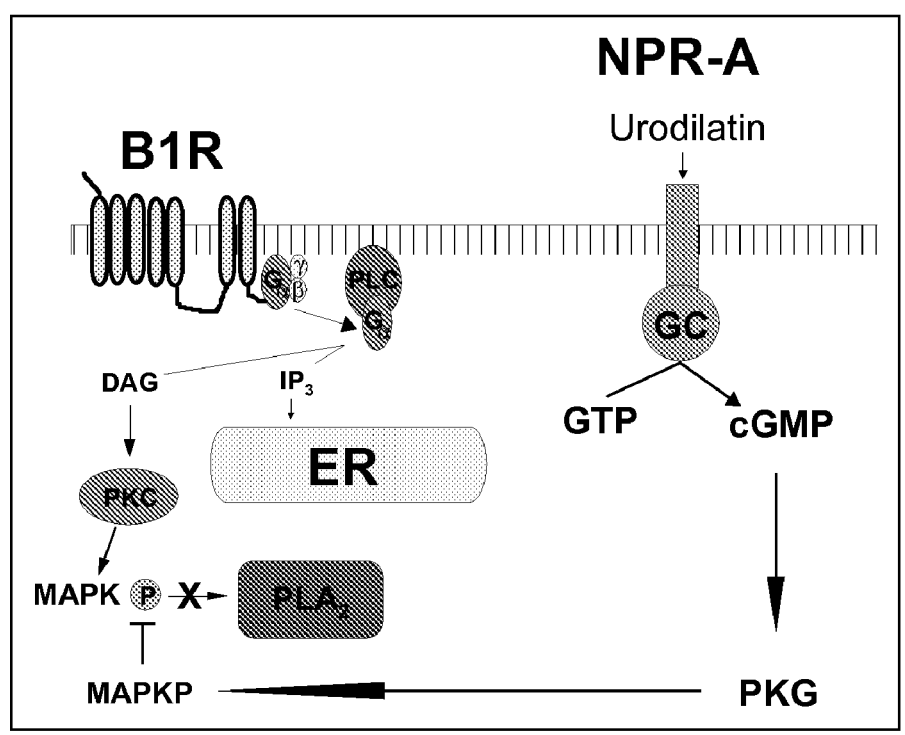
FIG. 4 is a schematic representation of how urodilatin blocks downstream signaling of the B1R bradykinin receptor through binding to the NPR-A receptor and activation of a cGMP-dependent protein kinase.

FIG. 4: Urodilatin blocks downstream signaling of the B1R bradykinin receptor through binding to the NPR-A receptor and activation of a cGMP-dependent protein kinase (PKG) which activates a MAPK phosphatase (MAPKP) and subsequently inhibits the MAPK signaling pathway.

Figure 5:
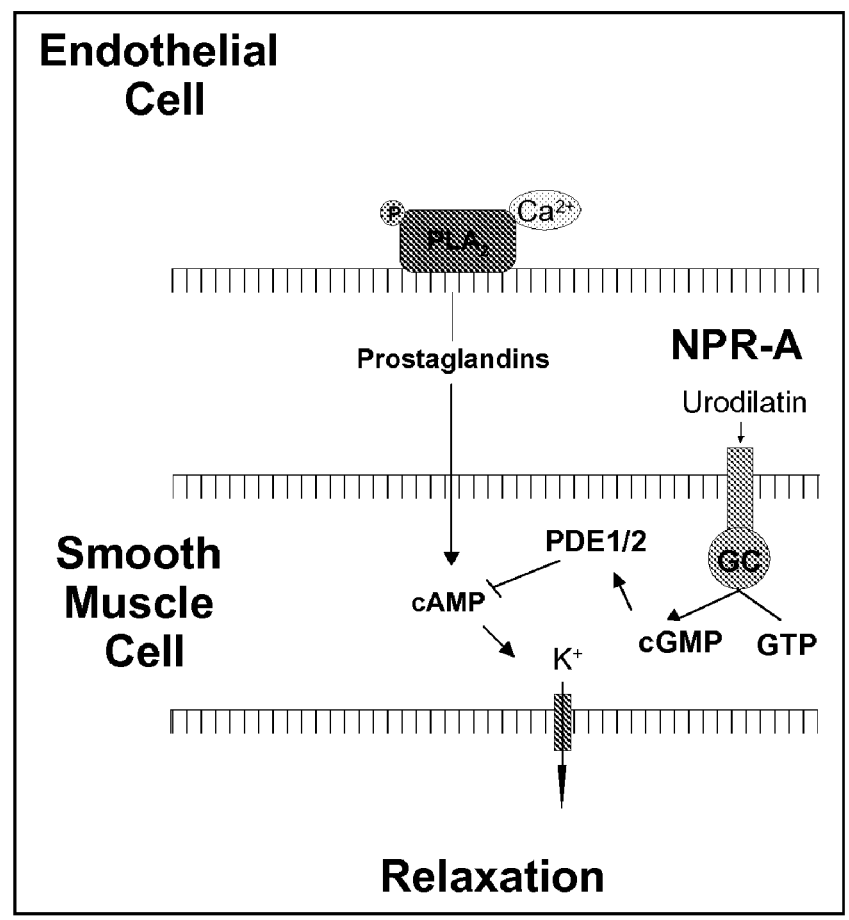
FIG. 5 is a schematic representation of how urodilatin blocks downstream signaling of bradykinin through binding to the NPR-A receptor and activation of cGMP-dependent protein phosphatases.

FIG. 5: Urodilatin blocks downstream signaling of bradykinin through binding to the NPR-A receptor and activation of cGMP-dependent protein phosphatases (PDE1/2) which deactivate cAMP and prevent smooth muscle relaxation.

The invention claimed is:

1. A method for the treatment of angioedema bradykinin-induced comprising administering a medicament containing a natriuretic peptide to an individual in need thereof.

2. The method of claim 1, wherein the natriuretic peptide is urodilatin.

3. The method of claim 1, wherein the natriuretic peptide is selected from the group consisting of ANP and BNP.

4. The method of claim 1, wherein the natriuretic peptide is selected from the group consisting of urodilatin, ANP and BNP.

5. The method of claim 1, wherein the natriuretic peptide is administered intravenously at the rate of about 7.5-60 ng/kg/min.

6. The method of claim 1, wherein the medicament further contains mannitol.

7. The method of claim 1, wherein the medicament is a solution further containing 3 to 10% mannitol.

8. The method of claim 1, wherein the medicament is a solution further containing 0.9% NaCl.

9. The method of claim 1, wherein the medicament is administered for a time period of at least 24 hours.

10. The method of claim 1, wherein the medicament is administered for a time period of 18 to 24 hours, or 24 to 72 hours, or for more than 72 hours.

11. The method of claim 1, wherein the angioedema is induced by administering inhibitors of angiotensin converting enzyme.

* * * * *